United States Patent [19]

Besseling et al.

[11] Patent Number: 5,047,641
[45] Date of Patent: Sep. 10, 1991

[54] SCINTILLATION CAMERA WITH AUTOMATICALLY COUNTERBALANCED GANTRY

[75] Inventors: Nicolaas C. Besseling, Schaumburg; Albrecht H. Enders, Chicago; George J. Hanz, Bloomingdale; Hendrik Koopmans, Schaumburg; David A. Yunder, Cicero, all of Ill.

[73] Assignee: Siemens Gammasonics, Inc., Hoffman Estates, Ill.

[21] Appl. No.: 493,566

[22] Filed: Mar. 14, 1990

[51] Int. Cl.⁵ .............................................. G01T 1/166
[52] U.S. Cl. ........................ 250/363.08; 250/363.05; 250/363.10
[58] Field of Search ...................... 250/363.08, 363.05, 250/363.04, 363.10

[56] References Cited

U.S. PATENT DOCUMENTS 4,692,625 9/1987 Hanz et al. ..................... 250/363.10
4,774,412 9/1988 Kurkake ........................ 250/363.08

Primary Examiner—Carolyn E. Fields
Assistant Examiner—Drew A. Dunn
Attorney, Agent, or Firm—Mark H. Jay

[57] ABSTRACT

The gantry of a scintillation camera is automatically counterbalanced about two parallel axes. One axis passes through the detector. The other axis is a tilt axis about which a gantry structure which supports the detector may be tilted. The gantry is also counterbalanced about an axis of rotation. A collimator may be detachably secured to the detector and automatically identified. The gantry is automatically adjusted to counterbalance it in accordance with the collimator which has been attached to the detector. In the preferred embodiment, the gantry is counterbalanced even when no collimator is secured to the detector.

14 Claims, 4 Drawing Sheets

SCINTILLATION CAMERA WITH AUTOMATICALLY COUNTERBALANCED GANTRY

BACKGROUND OF THE INVENTION

The present invention relates to a scintillation camera, and more particularly relates to the mechanical structure of such a camera. In its most immediate sense, the invention relates to apparatus which adapts the camera for attachment of a collimator.

A conventional scintillation camera such as a gamma camera includes a detector which converts into electrical signals gamma rays emitted from a patient after a radioisotope has been administered to the patient. The detector includes a scintillator and photodetectors. The gamma rays are directed to the scintillator (usually a crystal of thallium-doped sodium iodide) which absorbs the radiation and produces, in response, a minute flash of light. An array of photodetectors, which are placed in optical communication with the scintillation crystal, converts these flashes to electrical signals which are subsequently processed. After processing, the camera produces an image of that region of the patient from which the radiation was emitted.

Since the gamma radiation is emitted in all directions, it is necessary to collimate the radiation before the radiation is made incident upon the scintillation crystal. This is accomplished by using a collimator, which is a lead body perforated by relatively narrow channels. The collimator is detachably secured to the detector head, permitting the collimator to be changed so that, for example, the same camera can be used with different radioisotopes or different collimation patterns. A collimator may be quite massive, especially where it is intended for use with high-energy radioisotopes.

Where the gamma camera is used in SPECT (single photon emission computed tomography) to produce a three dimensional image of an organ being imaged, the detector is conventionally rotated about the patient. The detector is also moved when positioning it to reach a fixed position to produce a planar image. In both instances, it is conventionally necessary to counterbalance the detector so that the rotation/movement does not place excessive loads on the drive motors which are used to move the detector.

To avoid repeated rebalancing when substituting one collimator for another one of different weight, it is possible to equalize the weights of all collimators. Although this may optimize the balance of the scintillation camera, this optimization is achieved at the expense of image quality since the collimators cannot be optimized and the collimator is an important factor in image quality.

In a known scintillation camera manufactured by General Electric, the camera has a movable counterweight which can be moved by rotating a manually-operable crank. Such manual adjustment of the counterweight is, however, insufficient to attain precise balance, and also restricts the weight range of collimators which can be attached to the detector, since the counterweight can only be adjusted within relatively narrow limits.

It is also possible to use more powerful drive motors and sturdier drive mechanisms to avoid the need for adjustable counterbalancing of the detector. This has the disadvantage that the detector cannot be moved by hand. Such manual positioning of the detector is desirable as it permits more rapid and precise handling.

It is thus a general object of the present invention to provide an improved scintillation camera which does not suffer from these drawbacks.

One object of the invention is to provide a scintillation camera which places few constraints on the design of collimators which are to be used with it, thereby permitting the collimator design to be further optimized and providing improved results.

Another object is to provide a scintillation camera which can be manually moved even though it may be attached to collimators of widely different weights.

Still a further object is to provide a scintillation camera which will automatically counterbalance its gantry when the collimator is changed.

Yet another object is, in general, to improve upon known scintillation cameras.

In accordance with the invention, a scintillation camera with a gantry and a detector secured to the gantry has means for counterbalancing the gantry. Means are provided to detachably secure a collimator to the detector. The camera also has means for identifying the collimator which is so secured. A control means is connected to the identifying means and the counterbalancing means. The counterbalancing means is automatically adjusted so as to appropriately counterbalance the gantry in accordance with the collimator which is secured to the detector.

In further accordance with the invention, the counterbalancing means counterbalances the gantry with respect to two axes. Advantageously, one axis passes through the detector, and the other axis is parallel thereto.

In still further accordance with the invention, the gantry permits the detector to be rotated and is counterbalanced with respect to the axis of rotation. Thus, in the preferred embodiment, the gantry is counterbalanced with respect to three axes.

In preferred embodiments, the collimators which are designed for use in accordance with the invention are encoded using magnets, and Hall sensors in the detector head respond to the presence and absence of magnets to cause the counterbalancing mechanism in the camera to be appropriately adjusted.

Because there is an automatic readjustment of the camera gantry, the collimators which are designed for use with the camera are not constrained to fit within a narrow weight range. Also, the automatic readjustment of the gantry in response to the actual weight of the attached collimator makes it possible to so accurately counterbalance the camera that it can be easily moved by hand.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Throughout all the Figures, the same or corresponding elements are always indicated by the same reference numbers.

Figure 1:
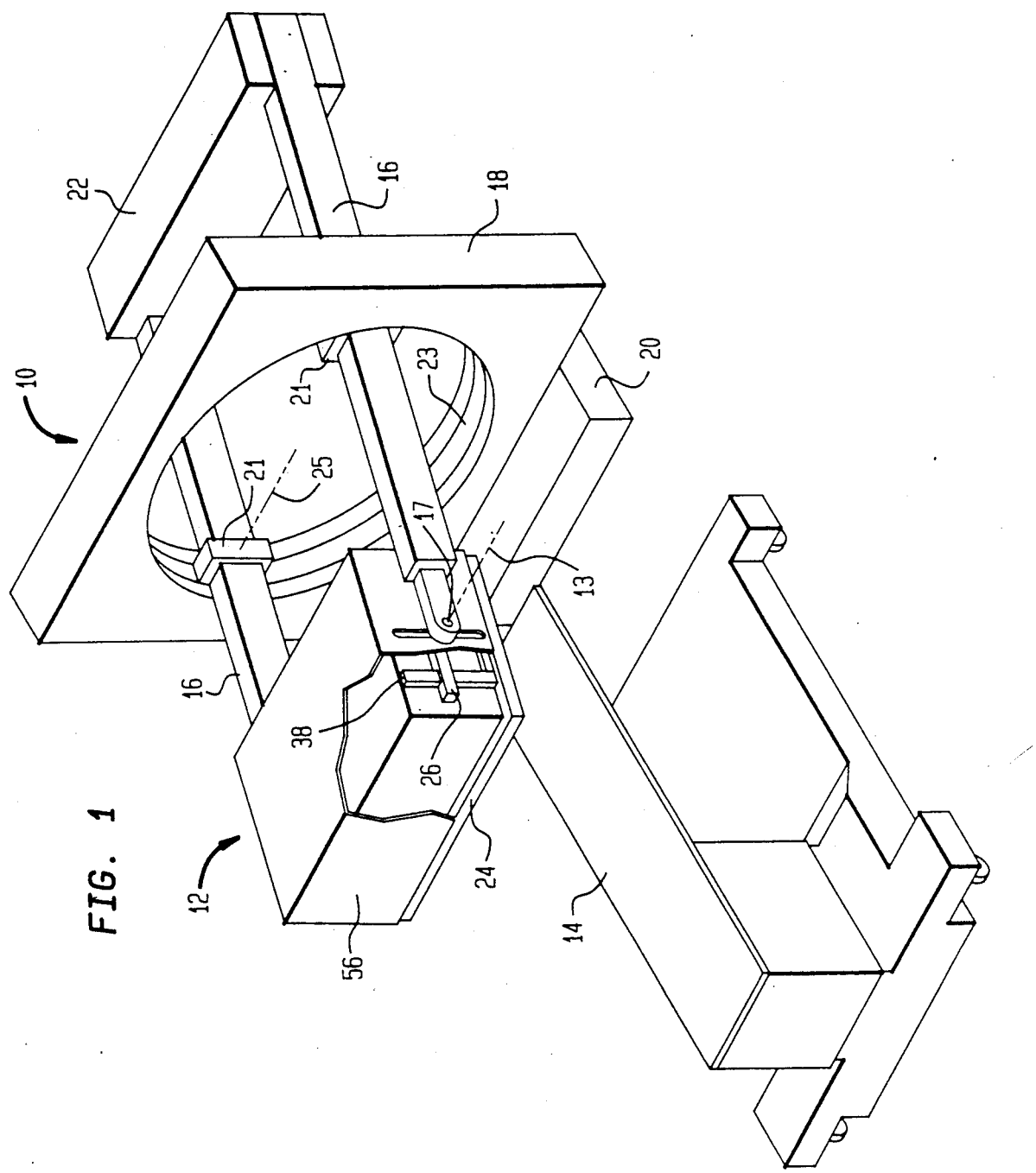
FIG. 1 is a perspective drawing of a preferred embodiment of the invention.

FIG. 1 shows a perspective view of a preferred embodiment of the invention, generally designated by reference numeral 10. The scintillation camera apparatus 10 includes a detector generally designated by reference numeral 12. The detector 12 is protected by a housing 56, and is positioned to conduct nuclear medicine studies of a patient (not shown) lying on a cantilever table 14. (The table 14 is not part of the invention and is only shown for the sake of illustration.)

Figure 5:
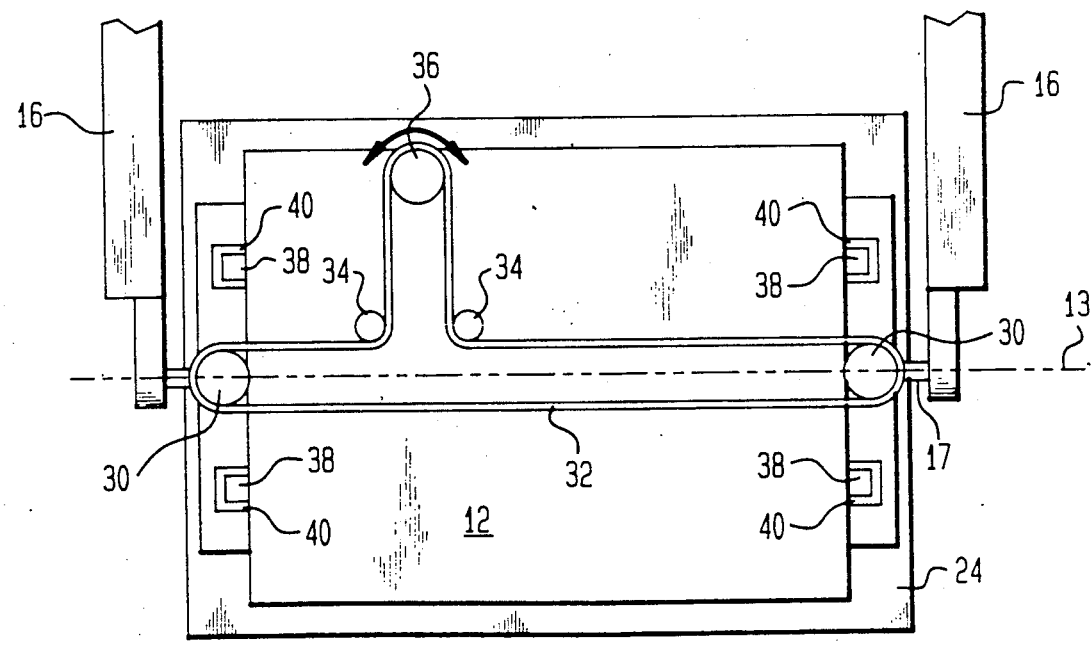
FIG. 5 is a schematic drawing of another part of the counterbalancing apparatus in the preferred embodiment.

The detector 12 is supported between the ends of a pair of parallel beams 16 so as to be rotatable on pivots 17 about an axis of rotation 13 (FIG. 5). A permanently affixed counterweight 22 is supported between the other ends of the beams 16, thereby counterbalancing the detector 12. The beams 16 are pivotally mounted intermediate their ends to a rotatable gantry ring 23 contained within a housing 18, the mounting being accomplished by yokes 21 so that the beams 16 can be tilted about a tilt axis 25 (which passes through the yokes 21). The gantry ring 23 is rotatable about plus or minus 360° (i.e. a total of two complete revolutions) in the vertical plane and is counterbalanced with respect to its axis of rotation as is described below. The beams 16 can be tilted by plus 44° or minus 30° with respect to the horizontal plane. Because the gantry ring 23 is counterbalanced with respect to its axis of rotation, it may be rotated manually; it may alternatively be rotated by a motor (not shown). Tilting of the beams 16 may be carried out manually as a result of the counterbalancing system which is described below. The entire apparatus is supported by a base 20, upon which rests the housing 18 and mechanisms contained therein.

To collimate gamma radiation (not shown) which leaves the patient before the radiation is incident upon the scintillator (not shown) contained within the detector 12, a collimator 24 is used. Each collimator 24 (only one is shown) is of a material which absorbs gamma radiation, and each has a large number of open-ended empty channels which face the patient at one end and the detector 12 at the other.

Typically, a hospital will own a plurality of collimators and the doctor or technician will select the one which is best suited for the study which is to be carried out. For example, where the radioisotope is of a high energy, a relatively massive collimator will be used. Alternatively, where an increased sensitivity is desired, as in the case of a study of the heart or brain, a conebeam or astigmatic collimator may be employed. Persons skilled in the art are aware that each detector 12 is equipped with devices which permit a collimator to be mounted to, and locked on, the detector; these devices are not part of the present invention and have been omitted from the drawings for the sake of clarity.

Ideally (i.e. where relatively few constraints in respect of weight and external dimensions are applied) collimators will vary greatly depending upon the applications for which they are designed. A high energy collimator which is designed for 360 keV gamma radiation can weigh almost 190 kg, while a low energy collimator designed for 140 keV radiation can weigh only 40 kg, i.e. less than one-fourth as much. Similarly, a high energy collimator may be designed to present a 7 cm thickness to incident radiation, while a low energy collimator may only present incident radiation with a 2.5 cm thickness or less. Consequently, if the detector 12 is to be easily moved by hand, greatly adjustable counterbalancing mechanisms must be employed to preserve counterbalancing of the detector 12 with whatever collimator may be employed. In the preferred embodiment, counterbalancing is accomplished with respect to three axes; axis 13 (through the detector 12, so that the detector can be manually pivoted on pivots 17), tilt axis 25 (so that the beams 16 may be tilted on the yokes 21) and the axis of rotation of the gantry ring 23 (so that the gantry ring 23 can be manually rotated about its axis). Counterbalancing with respect to axis 13 will be described first with reference to FIGS. 2 and 5.

Figure 2:
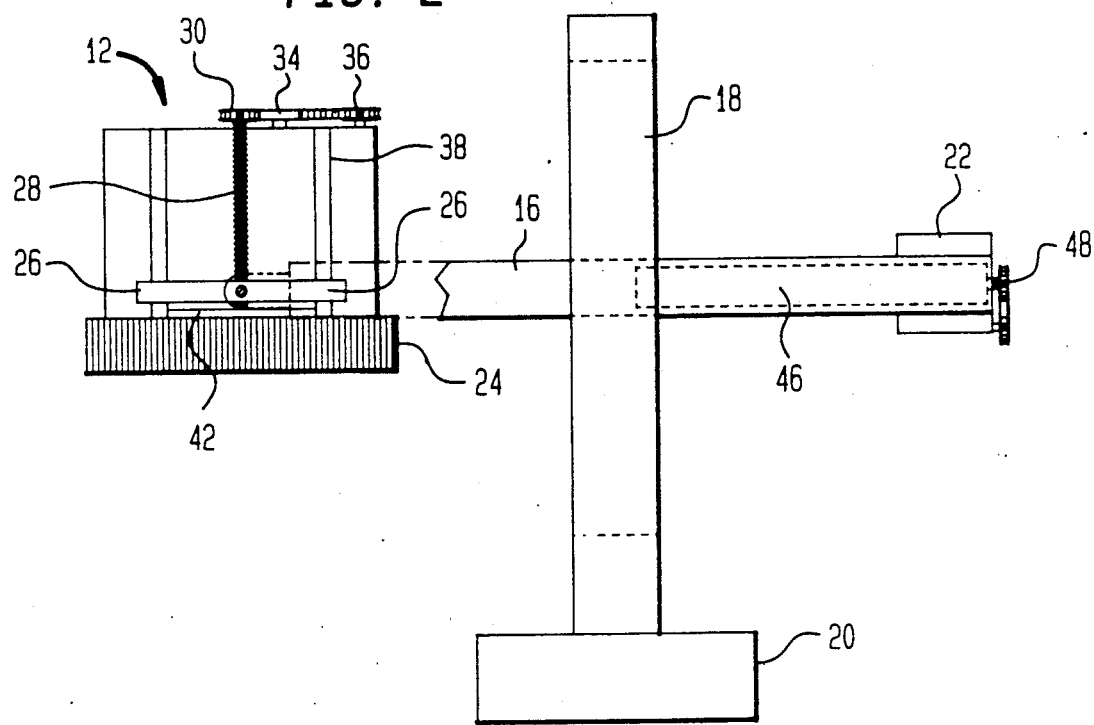
FIG. 2 is a side and partially detailed view of the preferred embodiment with a heavy collimator attached.

As is shown in FIGS. 2 and 5, the general counterbalancing principle is to move the detector 12 with respect to axis 13 until the center of gravity of the detector 12 with the collimator 24 attached is aligned with the axis 13. To do this, each pivot 17 of the beams 16 is fixed to a drive nut 26. The drive nuts 26 are parallel to each other and extend parallel to the collimator 24 along the shorter sides of the detector 12. Each drive nut 26 is engaged by a threaded screw 28 which extends perpendicular to its corresponding drive nut 26; the screws 28 are parallel and are fixed to the detector 12 at their ends in such a manner as to permit them to be rotated. Such rotation is accomplished by the use of a chain drive mechanism.

The chain drive mechanism includes a sprocket wheel 30 which is attached to each screw 28 at its end which is remote from the collimator 24. The sprocket wheels 30 are engaged by a chain 32 which is parallel to the collimator 24 and is located on the opposite side of the detector 12. The chain 32 is driven by a computer-controlled first motor 128 (not shown physically, but shown electrically in FIG. 6); the first motor 128 rotates a sprocket 36 which engages the chain 32 and causes it to move in either direction (as shown by the arrow in FIG. 5). The chain 32 is maintained in position by two sprocket wheels 34 which are located on either side of the sprocket 36 and which act as idlers.

In order to insure that the detector 12 can only move parallel to the axes of the screws 28, each drive nut 26 is engaged by, and guided by, two guide bars 38. Each pair of guide bars 38 is parallel to and located on either side of the corresponding screw 28 and passes through a linear bearing 40 which is mounted to the drive nut 26.

Thus, to counterbalance the detector head 12 in such a manner as to compensate for differences in collimators 24, the first motor 128 is rotated in the appropriate direction. This moves the chain 32, which rotates the sprocket wheels 30 and the screws 28, causing the detector 12 to slide along the four guide bars 38 with respect to the drive nuts 26. Movement continues until the center of gravity of the detector/collimator assembly is aligned with the axis 13.

Counterbalancing with respect to tilt axis 25 will now be discussed with reference to FIGS. 1, 3 and 4. As a preliminary matter, it will be understood that the detector 12 is quite heavy, even without a collimator 24 attached to it. This is the reason why the counterweight 22 (in the preferred embodiment, a massive steel beam) is attached to the ends of the beams 16. The adjustable counterbalancing described below compensates for variability in the weights of the collimators 24 which may be secured to the detector 12.

Figure 3:
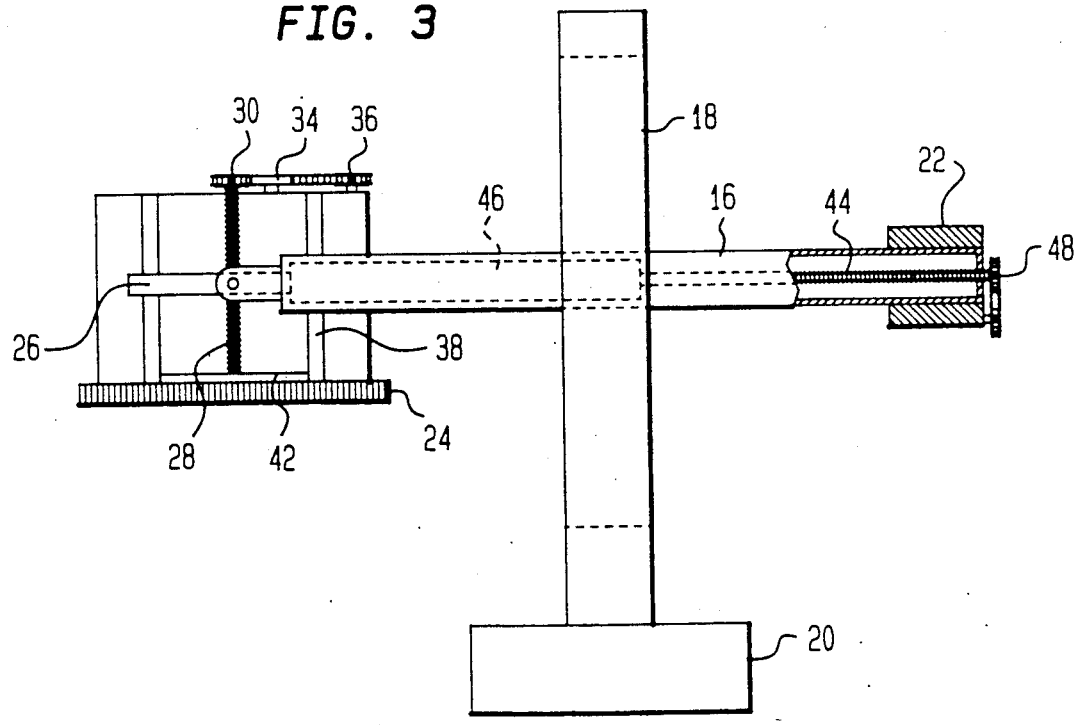
FIG. 3 is a side and partially detailed and sectional view of the preferred embodiment with a lighter collimator attached.
Figure 4:
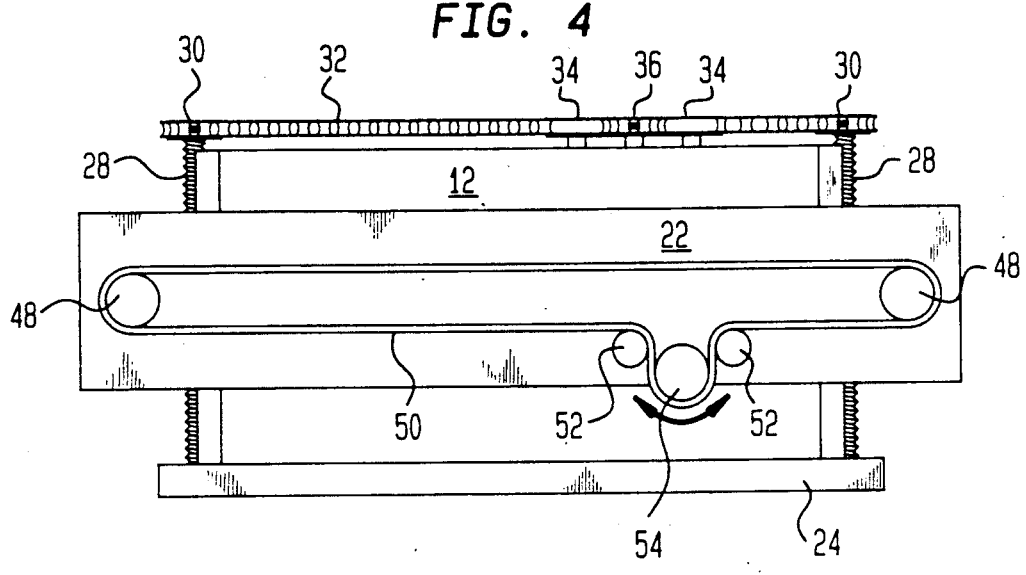
FIG. 4 is a schematic drawing of one part of the counterbalancing apparatus in the preferred embodiment.

As illustrated in FIG. 3, each beam 16 is hollow and accommodates a power transmission screw 44; the screws 44 are fixed at their ends to the beams 16 in such a manner that they are rotatable. The screws 44 are advantageously acme screws, and they extend along the axes of the beams 16. Each screw 44 supports and threadedly engages a counterweight 46. In the preferred embodiment, each counterweight 46 is a lead cylinder. The counterweights 46 are so mounted that they do not rotate within the beams 16, so that when the screws 44 are rotated, the counterweights 46 are axially shifted within their corresponding beams 16.

The screws 44 are rotated by a chain drive. Each screw 44 extends beyond the rear end of the beam 16 and is connected to a sprocket wheel 48. As can best be seen in FIG. 4, a chain 50 drives the sprocket wheels 48. The chain 50 is driven by a computer-controlled second motor 130 (not shown physically, but shown electrically in FIG. 6) which rotates a sprocket 54 in either direction (as is shown by the arrows in FIG. 4.) The chain 50 is maintained in position by sprocket wheels 52 which are located on either side of the sprocket 54 and which act as idlers.

Thus, to counterbalance the detector 12 with respect to tilt axis 25 as a result of differences between the weights of collimators 24 which may be utilized, the second motor 130 is rotated in the appropriate direction. This rotates the sprocket 54, the sprocket wheels 48 and the screws 44, causing the counterweights 46 to be shifted within the beams. This shifting continues until the detector 12 is counterbalanced with respect to tilt axis 25.

While it is not evident from the Figures, counterbalancing of the gantry about the axis of rotation of the gantry ring 23 is also accomplished using the above-described apparatus. This is accomplished by so choosing the dimensions and weights of the various components that a line connecting the center of gravity of the detector 12 and collimator 24 with the center of gravity of the counterweights 22 and 46 always passes through the center of the gantry ring 23. Thus, regardless of the weight of the collimator 24 which may be used, the gantry ring 23 will be manually rotatable.

As discussed above, in accordance with the invention the scintillation camera gantry is automatically counterbalanced in accordance with the weight of the particular collimator 24 which has been selected. In the preferred embodiment, this is carried out by encoding each collimator 24 in such a way that the detector 12 can register its identity. In the preferred embodiment, the encoding is magnetic, but this is not necessary; other encoding techniques can be used instead.

Advantageously, each collimator 24 is encoded with a seven bit code at the factory; the encoding represents the position to which the axis 13 must be moved to properly counterbalance the detector 12 (and thus represents the position to which the counterweights 46 must be moved to counterbalance the gantry with respect to the tilt axis 25). The seven bits (more or fewer bits may be used and the number of bits is not a part of the invention) are represented by seven predetermined locations on each collimator 24, and at each location a 1 or a 0 is represented by the presence or absence of a small magnet. An array 42 of magnetic sensors, which may advantageously be Hall sensors, is mounted to the detector 12 in such a manner that each sensor will be directly adjacent its corresponding one of the seven locations on the collimator 24. The information represented by the magnets on the collimator 24 is thus read at the detector 12 and the counterbalancing of the gantry is correspondingly adjusted. The collimator 24 shown in FIG. 2 is heavier than is the collimator 24 shown in FIG. 3; as a result, the counterweights 46 are closer to the detector 12 in the FIG. 3 case than they are in the FIG. 2 case. Likewise, the detector 12 is shifted higher with respect to the pivots 17 in the FIG. 2 case than it is in the FIG. 3 case.

In the preferred embodiment, the gantry is so designed that it is counterbalanced, and therefore manually moveable, even when no collimator 24 is secured to the detector 12. This facilitates calibration of the detector 12; calibration is accomplished in the absence of a collimator 24.

It will be appreciated by persons skilled in the art that the gantry must contain much mechanical apparatus which does not appear in the foregoing Figures. For example, all the movable parts must be equipped with "fail-safe" brakes which apply in the event of power failure and which positively prevent motion unless released, and limit switches, position sensors etc. are necessary to prevent damage to the apparatus or injury to the patient in the event of improper operation or equipment malfunction. However, this apparatus, like much other necessary apparatus, is not part of the invention, and has been omitted from the Figures for the sake of simplicity.

Additionally, persons skilled in the art will understand that the table 14 is connected with the mechanism just described because it is often necessary to synchronize motion of the table 14 with motion and absence of motion of the camera gantry. In fact, electrical connections exist between the table 14 and the gantry so that both systems may be operated under common control. However, these connections, and the circuitry and electromechanical structure associated with them, have been omitted from the Figures for the sake of simplicity since it is not a part of the present invention.

Figure 6:
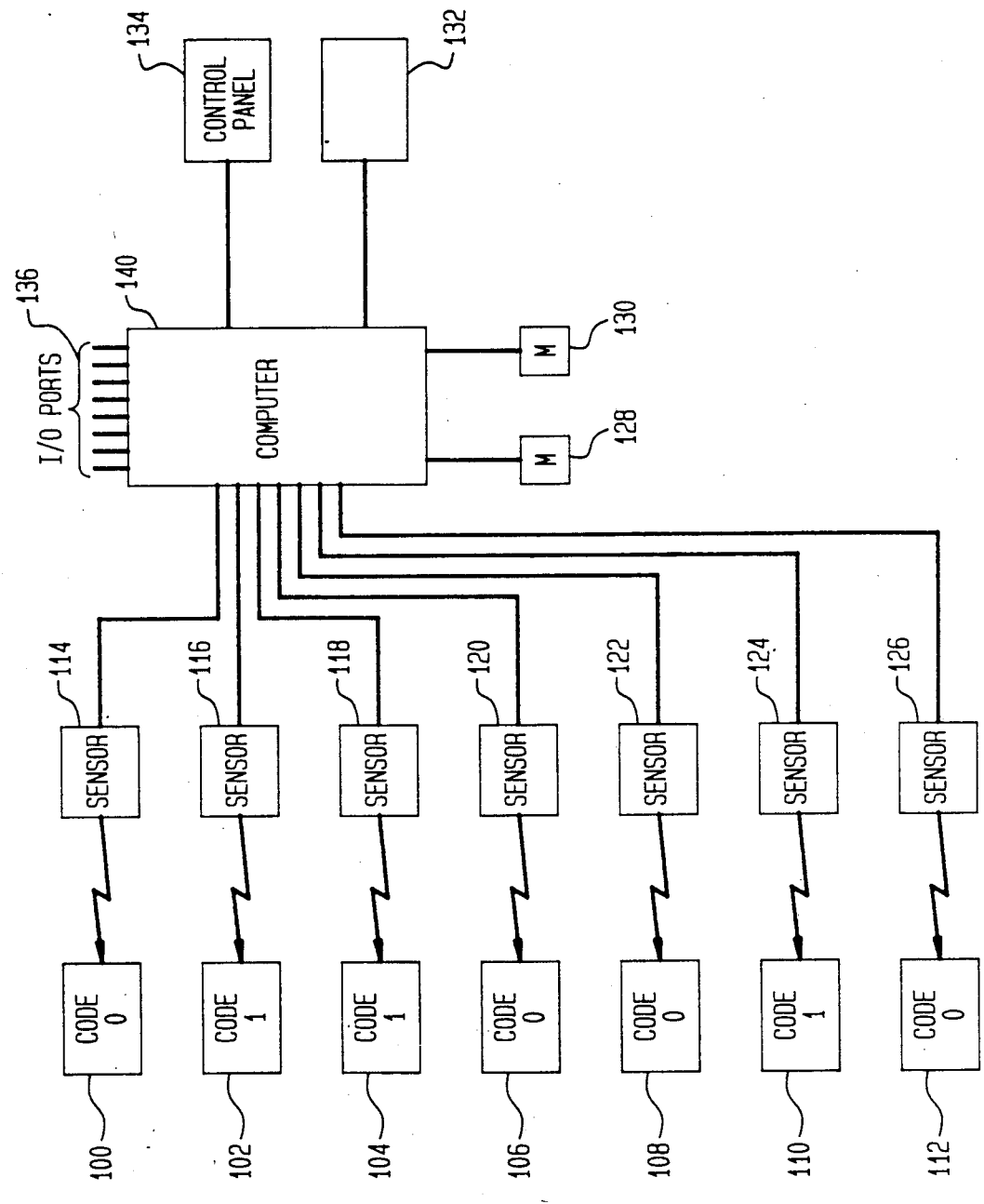
FIG. 6 is a partially schematic block diagram showing various nonmechanical parts of the preferred embodiment.

The nonmechanical components in the preferred embodiment are shown in more detail in FIG. 6. On each collimator 24, there are seven regions 100, 102, 104, 106, 108, 110 and 112. The presence or absence of a magnet at each of these locations indicates a 1 or a 0 respectively; in this illustrative example, there are magnets at regions 102, 104 and 110. The corresponding regions on the detector 2 have Hall sensors 114, 116, 118, 120, 122, 124, and 126, which as a group form the array 42. The array 42 is connected to an on-board computerized controller 140 (which advantageously includes two computers, not shown, one for each of the motors 128 and 130). The controller 140 is connected to the first motor 128 and the second motor 130, as well as to appropriate other electromechanical mechanisms such as shaft encoders, brakes, limit switches, position sensors etc. which are collectively indicated by reference numeral 132. (Shaft encoders, not shown specifically, are advantageously used to monitor the positions of the shafts of the motors 128 and 130.) The controller 140 is also connected to a control panel indicated by reference numeral 134 and to various I/O ports collectively indicated by reference numeral 136. The ports 136 provide for, e.g., connections to the table 14, connection to hand-operated controls (not shown), connection to a computer (not shown), etc.

When a doctor or technician wishes to change the collimator 24 which is attached to the detector 12, the table 14 is moved out of the way and the detector 12 is moved over a collimator cart (not shown) on which the installed collimator is to be deposited. After the camera has been moved to an appropriate position and the appropriate switches, sensors etc. 132 are in states which indicate that the collimator 24 may be released from the detector 12 (as for example by an interaction between the collimator cart and a proximity switch on the detector 12) the collimator 24 is released, leaving it on the cart. The gantry counterbalancing is adjusted as necessary by operating the motors 128 and 130 under the control of the controller 140, the appropriate brakes etc. are released and the detector 12 is then moved over the next collimator 24 which is to be installed on the detector 12. Once appropriate positioning of the detector 12 has been verified, the collimator 24 may be attached to the detector 12. At this juncture, the array 42 of Hall sensors responds to whatever magnets are located at the seven locations 100 - 112, the controller 140 operates the motors 128 and 130, and the gantry counterbalancing is appropriately adjusted so that appropriate counterbalancing exists between axes 13 and 25.

Those skilled in the art will understand that changes can be made in the preferred embodiments here described, and that these embodiments can be used for other purposes. Such changes and uses are within the scope of the invention, which is limited only by the claims which follow.

We claim:

1. A scintillation camera, comprising:
    a gantry;
    a detector secured to the gantry;
    means for detachably securing a collimator to the detector;
    means for counterbalancing the gantry;
    means for identifying a collimator which has been secured to the detector; and
    control means operatively connected to said counterbalancing means and said identifying means and causing said counterbalancing means to be automatically adjusted so as to appropriately counterbalance the gantry in accordance with the collimator which has been secured to the detector.

2. The camera of claim 1, wherein said counterbalancing means counterbalances the gantry with respect to two axes.

3. The camera of claim 2, wherein said counterbalancing means counterbalances the gantry with respect to two parallel axes.

4. The camera of claim 3, wherein one of said axes passes through the detector.

5. The camera of claim 2, wherein the gantry is rotatable about a third axis of rotation.

6. The camera of claim 1, further including at least one collimator which is adapted for detachable securement to the detector.

7. The camera of claim 1, wherein said identifying means comprises an array of Hall effect sensors.

8. The camera of claim 1, wherein said control means comprises a computerized controller.

9. The camera of claim 1, wherein the detector is secured to the gantry in such a manner as to be pivotable about an axis and said counterbalancing means counterbalances the detector with respect to said axis.

10. The camera of claim 9, wherein said counterbalancing means moves the detector and any collimator attached thereto in such a manner as to align a center of gravity of said detector and collimator with said axis.

11. The camera of claim 1, wherein the detector is secured to an end of a tiltable gantry structure and said counterbalancing means counterbalances said tiltable gantry structure about a tilt axis.

12. The camera of claim 11, wherein said tiltable gantry structure comprises a pair of hollow beams and said counterbalancing means comprises a pair of weights which are contained in and shiftable within said pair of beams.

13. The camera of claim 11, wherein the gantry structure is rotatable about an axis of rotation and is counterbalanced about said axis of rotation.

14. The camera of claim 1, wherein said control means operates in such a manner that when no collimator is secured to the detector, the counterbalancing means is automatically adjusted so as to appropriately counterbalance the gantry.

* * * * *

UNITED STATES PATENT AND TRADEMARK OFFICE
CERTIFICATE OF CORRECTION

PATENT NO. : 5,047,641

DATED : September 10, 1991

INVENTOR(S) : Besseling, et. al.

It is certified that error appears in the above-identified patent and that said Letters Patent is hereby corrected as shown below:

On the Title page

Item [75], misspelling of the last name of the last-name inventor--

David A. Yunker-- as "Yunder".

Signed and Sealed this

Twenty-sixth Day of January, 1993

Attest:

DOUGLAS B. COMER

*Attesting Officer*  *Acting Commissioner of Patents and Trademarks*